United States Patent [19]

Matsumoto et al.

[11] Patent Number: 5,177,237
[45] Date of Patent: Jan. 5, 1993

[54] HYDRAZINE DERIVATIVES USEFUL AS INTERMEDIATES IN THE SYNTHESIS OF HYPOTENSIVE AGENTS

[75] Inventors: Hiroo Matsumoto; Kiyotomo Seto; Ryozo Sakoda, all of Funabashi, Japan

[73] Assignee: Nissan Chemical Industries Ltd., Tokyo, Japan

[21] Appl. No.: 783,103

[22] Filed: Oct. 24, 1991

[30] Foreign Application Priority Data

Nov. 15, 1990 [JP] Japan .................................. 2-310074
Aug. 22, 1991 [JP] Japan .................................. 3-210696

[51] Int. Cl.⁵ .............................................. C07F 9/6574
[52] U.S. Cl. ........................................ 558/77; 558/83
[58] Field of Search .................................... 558/77, 83

[56] References Cited

U.S. PATENT DOCUMENTS 4,879,400  11/1989  Seto et al. ............................ 558/83
4,885,284  12/1989  Seto et al. ........................... 558/178

FOREIGN PATENT DOCUMENTS 62-226991  10/1987  Japan ..................................... 558/83
62-226992  10/1987  Japan .

OTHER PUBLICATIONS

Yamasaki, T. et al., J. Chem. Soc. Perkin Trans. 1 1991, (5), 991–6.
Schweizer, E. E. et al., J. Org. Chem. 1987, 52, 1810–1816.
Pratapan, S. et al., J. Org. Chem. 1986, 51, 1972–1976.
March, J., Advanced Organic Chemistry; Third Edition; John Wiley and Sons: New York, 1985; pp. 689–691.

*Primary Examiner*—Mary C. Lee
*Assistant Examiner*—Michael G. Ambrose
*Attorney, Agent, or Firm*—Oblon, Spivak, McClelland, Maier & Neustadt

[57] ABSTRACT

A hydrazine derivative having the formula:

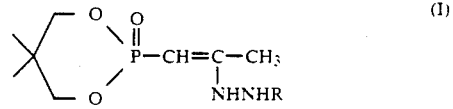

wherein R is a hydrogen atom or

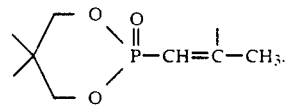

3 Claims, No Drawings

HYDRAZINE DERIVATIVES USEFUL AS INTERMEDIATES IN THE SYNTHESIS OF HYPOTENSIVE AGENTS

The present invention relates to hydrazine derivatives of the following formula I which are novel intermediates for a dihydropyridine derivative having the following formula V useful for medicines for curing hyper-tension, a process for their production and a process for producing an acetonyl cyclic phosphonate having the following formula IV which is an important intermediate for the dihydropyridine derivative by using the hydrazine derivatives.

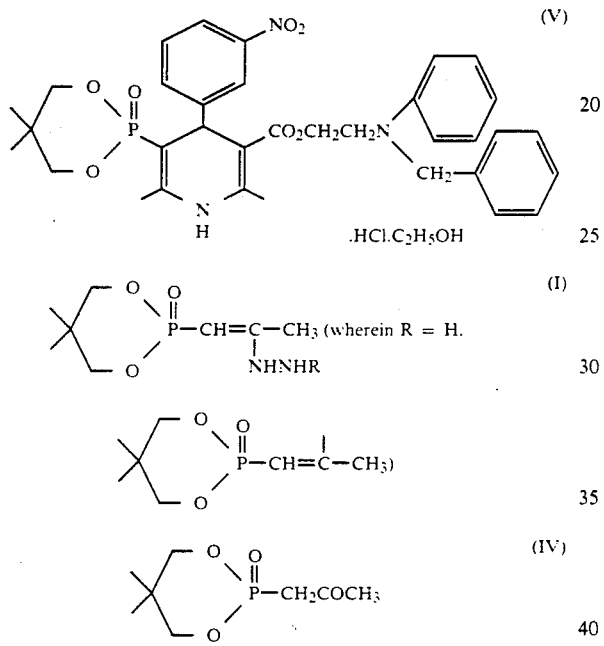

The dihydropyridine derivative having the formula V can be readily produced from the acetonyl cyclic phosphonate having the formula IV. Therefore, the present invention is useful to provide excellent raw materials for medicines.

An acetonyl cyclic phosphonate is usually produced by Arbuzov reaction between a cyclic phosphite and a haloacetone (for example, European Patent Publication No. 159040/1985).

The acetonyl cyclic phosphonate of the formula IV can be produced, for example, by Arbuzov reaction as follows:

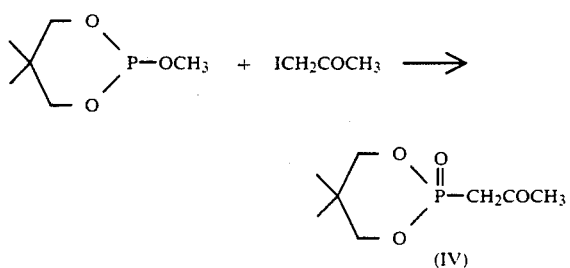

However, as drawbacks of the Arbuzov reaction,
① Perkow reaction occurs as side-reaction;
② An alkyl halide formed during the reaction, is reacted with a cyclic phosphite to produce an alkyl phosphonate; and
③ A haloacetone is lachrymatory; may be mentioned.

Therefore, the Arbuzov reaction is not appropriate as a process for industrial application, and it has been desired to develop a simpler and more effective process.

Further, Morel et al. reported a process wherein compounds having the following formula VI and VII are synthesized by reacting amines with allenyl cyclic phosphonate (C. R. Hebd. Seances Acad. Sci., Ser. C280(7), 473–6, (1975)). However, the process requires a long period of time.

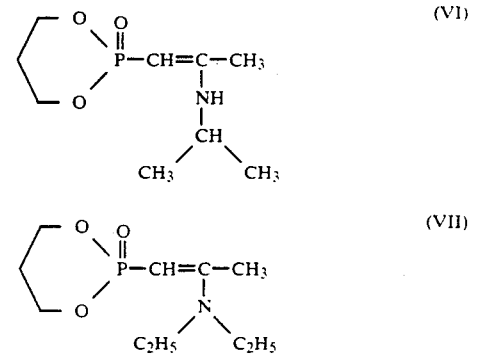

Under the circumstances, the present inventors have conducted extensive researches to solve the above problems and arrived at the present invention wherein hydrazine which has a molecular weight smaller than amines and is economical, is used. Namely, the present invention provides (1) a hydrazine derivative having the formula I;

(2) a process for producing a hydrazine derivative having the formula I, which comprises reacting hydrazine with an allenyl cyclic phosphonate having the following formula II and/or a propynyl cyclic phosphonate having the following formula III:

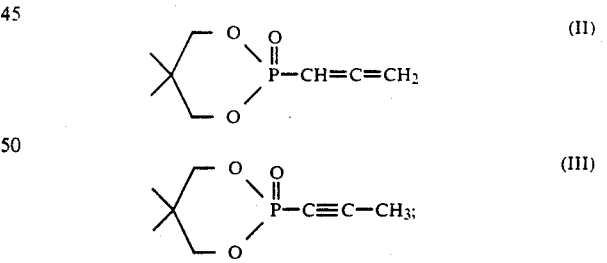

(3) a process for producing an acetonyl cyclic phosphonate of the formula IV, which comprises subjecting a hydrazine derivative having the formula I to acid hydrolysis; and (4) a process for producing an acetonyl cyclic phosphonate of the formula IV, which comprises reacting hydrazine with an allenyl cyclic phosphonate of the formula II and/or a propynyl cyclic phosphonate of the formula III, followed by acid hydrolysis.

Here, the hydrazine derivative having the formula I includes cis-trans isomers and tautomers represented by the following formulas I' and I":

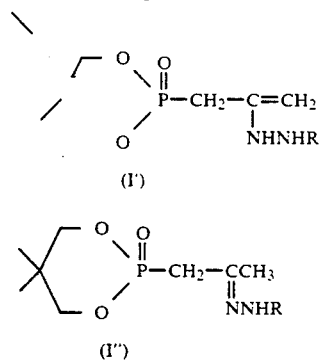

(I')

(I'')

The raw materials for the allenyl cyclic phosphonate having the formula II and/or the propynyl cyclic phosphonate having the formula III to be used in the present invention can be readily prepared by reacting chlorophosphite and propargyl alcohol in the presence of triethylamine, followed by heating. (J. Am. Chem. Soc., 72, 5491 (1950); ibid, 92, 7125 (1970)) (cf. Reference Example 1).

The hydrazine derivative of the formula I is produced by dissolving the allenyl cyclic phosphonate of the formula II and/or the propynyl cyclic phosphonate of the formula III in a nitrile type solvent such as acetonitrile, an aromatic hydrocarbon type solvent such as benzene and toluene, an ether type solvent such as tetrahydrofuran and dioxane, a halogen type solvent such as chloroform and dichloromethane, an ester type solvent such as ethyl acetate, an amide type solvent such as dimethylformamide, an alcohol type solvent such as methanol and ethanol and a solvent such as dimethylsulfoxide and water, and adding hydrazine thereto. As hydrazine, its monohydrate is the most convenient, for example, from the handling viewpoint. However, anhydrous hydrazine and hydrazine having a ratio of hydrazine to water different from that of its monohydrate can be used. Further, hydrazine released from a hydrochloride or a sulfate of hydrazine in the reaction system may be used for the reaction. If the amount of hydrazine used is less than 0.3 mol per 1 mol of the allenyl cyclic phosphonate of the formula II and/or the propynyl cyclic phosphonate of the formula III, the yield of the desired product will be naturally poor. On the other hand, if hydrazine is used in large excess, it affects the next step of acid hydrolysis. Thus, hydrazine is used in amount of from 0.3 to 5.0 mols, preferably from 1.0 to 2.0 mols per mol of the allenyl cyclic phosphonate of the formula II and/or the propynyl cyclic phosphonate of the formula III.

The reaction of the allenyl phosphonate with hydrazine is completed in a few minutes when hydrazine is used at least 1 mol per mol of the allenyl phosphonate and within one hour when hydrazine is used from 0.5 to 1 mol per mol of the allenyl phosphonate.

The reaction temperature may be in a range of from $-20°$ C. to the boiling point of the solvent, usually from $-10°$ to $90°$ C., preferably from $0°$ to $50°$ C.

Furthermore, when the raw material of the allenyl cyclic phosphonate of the formula II is produced, the propynyl cyclic phosphonate of the formula III is simultaneously produced (Tet. Lett., 1971, 1937). It is not required to separate them because both compounds are used for the production of the acetonyl cyclic phosphonate of the formula IV as described above (cf. Example 7).

The hydrazine derivative of the formula I can be converted to the desired product of the acetonyl phosphonate having the formula IV by dissolving or suspending in a solvent soluble to water such as acetonitrile, acetone and alcohols and then adding an aqueous acidic solution thereto. As the acid to be used here, an organic acid such as acetic acid and oxalic acid may be used in addition to a mineral acid such as hydrochloric acid and sulfuric acid. The amount of the acid used is required to be at least such an amount as to neutralize hydrazine formed (e.g. 2 time mols in the case of hydrochloric acid). Even if the acid is used in excess there is no particular problem to the reaction. Thus, the amount of the acid used is in a range of from 1 to 100 mols, preferably from 2 to 30 mols per mol of hydrazine formed.

The amount of water used is required to be at least an amount consumer in the hydrolysis (equimol or 2 time mols). However, even if it is used in excess, there is no particular problem to the reaction. Thus, the amount of water used is usually in a range of from 0.5 to 5,000 time mols, preferably from 1 to 500 time mols.

The reaction temperature may be in a range of from $-20°$ C. to the boiling point of the solvent, usually from $-10°$ to $50°$ C. and preferably from $0°$ to $30°$ C.

According to the present invention, haloacetone which is lachrymatory is not used, and the yields of the desired products are excellent because no Perkow reaction proceeds or no alkyl halide is produced, whereby the present invention is superior to Arbuzov reaction.

Now, the present invention will be described in further detail with reference to the Examples. However, it should be understood that the present invention is by no means restricted by such specific Examples.

REFERENCE EXAMPLE 1

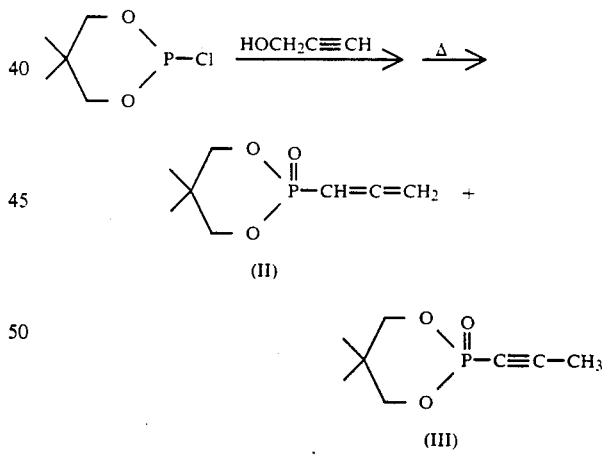

571 g (10.2 mol) of propargyl alcohol and 858 g (8.48 mol) of triethylamine were dissolved in 8.34 kg of acetonitrile, and 1,423 g (8.44 mol) of 2-chloro-5,5-dimethyl-1,3,2-dioxaphosphorinane was dropwise added thereto under stirring and cooling with ice. After the completion of dropwise addition, the mixture was stirred further for one hour under cooing with ice, and returned to room temperature and stirred further for 4 hours. Triethylamine hydrochloride thus precipitated was removed by filtration by means of suction and washed with 1.16 kg of acetonitrile. The wash liquid and the filtrate were combined and refluxed for 2 hours under heating to distill off 4.7 kg of acetonitrile, whereby an acetonitrile solution of mixture of 2-allenyl-5,5-dimethyl-2-oxo-1,3,2-dioxaphosphorinane (II) and 5,5-dimethyl-2-(1-propynyl)-2-oxo-1,3,2-dioxaphosphorinane (III) was obtained.

REFERENCE EXAMPLE 2

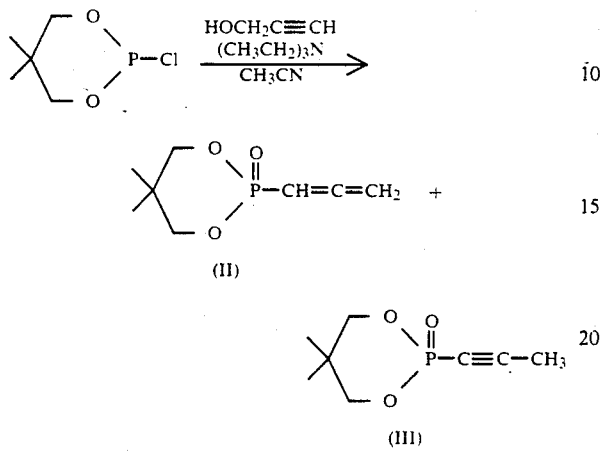

5.38 g (96.0 mmol) of propargyl alcohol and 8.08 g (79.8 mmol) of triethylamine were dissolved in 100 ml of acetonitrile, and 13.4 g (79.5 mmol) of 2-chloro-5,5-dimethyl-1,3,2-dioxaphosphorinane was dropwise added under stirring and cooling with ice. After the completion of dropwise addition, the mixture was stirred for one hour as it was. Then, the mixture was returned to room temperature and stirred further for 4 hours. The reaction solution was subjected to filtration to remove triethylamine hydrochloride formed, and the filtrate was refluxed for 2 hours under heating. The reaction solution was concentrated under reduced pressure and the residue was dissolved in chloroform, followed by washing, drying over anhydrous sodium sulfate. The solvent was distilled off. Diethyl ether was added to the residue for recrystallization and subjected to filtration to obtain 6.95 g (yield: 46.5%) of 2-allenyl-5,5-dimethyl-2-oxo-1,3,2-dioxaphosphorinane (II) as light yellow-brown crystal.

Melting point: 128°–133° C.

Further, the filtrates were combined and the solvent was distilled off. The residue was subjected to silica gel chromatography to obtain 2.63 g (yield: 17.6%) of 5,5-dimethyl-2-(1-propynyl)-2-oxo-1,3,2-dioxaphosphorinane (III).

Melting point: 72°–77° C.

EXAMPLE 1

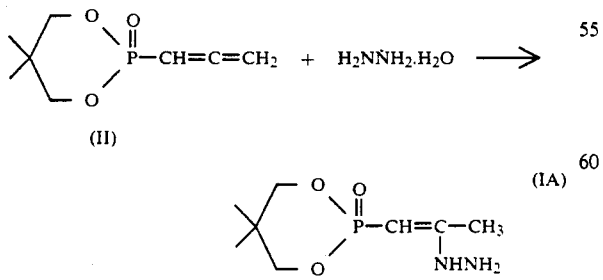

0.35 g (1.9 mmol) of 2-allenyl-5,5-dimethyl-2-oxo-1,3,2-dioxaphosphorinane (II) was dissolved in 2 ml of acetonitrile, and 0.15 g (3.0 mmol) of hydrazine monohydrate was added thereto and stirred for 30 minutes at room temperature. The solvent was distilled off and the oily residue was dried by means of a vacuum pump, whereby crystallization occurred and a colorless crystal was quantitatively obtained (0.42 g).

The reaction product was a hydrazine derivative having the formula IA.

Elemental analysis:
Theoretical value C 43. 63%, H 7. 78%, N 12. 72%;
Analytical value C 43. 60%, H 7. 89%, N 12. 58%.
Mass spectrum: 220 (92, M+), 135 (100)

EXAMPLE 2

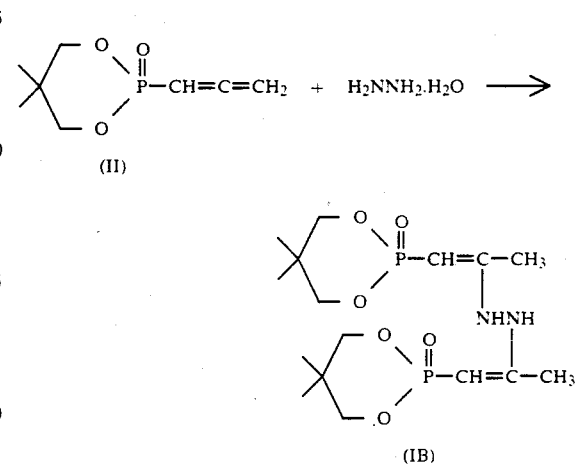

0.69 g (3.7 mmol) of 2-allenyl-5,5-dimethyl-2-oxo-1,3,2-dioxaphosphorinane (II) was dissolved in 3 ml of acetonitrile and 0.09 g (1.8 mmol) of hydrazine monohydrate was added thereto. The mixture was left for 30 minutes, and 0.05 g (1.0 mmol) of hydrazine monohydrate was further added and left for 30 minutes at room temperature. When precipitation of a crystal was observed, the mixture was moved in a refrigerator and left for overnight. Then, the crystal was collected by filtration and washed with 1 ml of acetonitrile and dried to obtain 0.24 g (yield: 32%) of colorless crystal.

Melting point: 214°–216° C.

The reaction product was the compound having the formula IB.

Elemental analysis:
Theoretical value C 47. 06%, H 7. 40%, N 6. 86%;
Analytical value C 47. 07%, H 7. 40%, N 6. 76%.
Mass spectrum: 408 (62, M+), 109 (100)

EXAMPLE 3

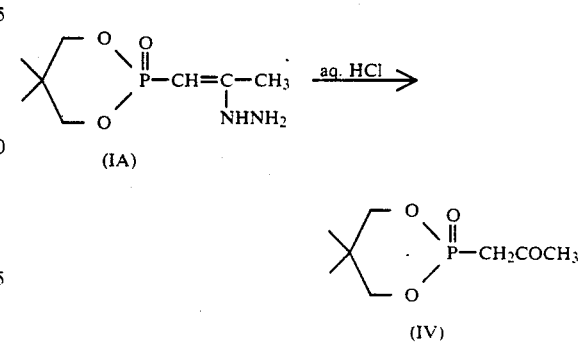

110 mg (0.500 mmol) of the hydrazine derivative (IA) as in Example 1 was suspended in 1.1 g of acetonitrile, and dissolved by addition of 2.2 g of 10% by weight hydrochloric acid. The mixture was left for one hour. The reaction mixture diluted with 30 ml of 20% by weight sodium chloride aqueous solution, was extracted 2 times by 30 ml of chloroform. The chloroform layers were combined and dried over anhydrous sodium sulfate, followed by filtration. The solvent was distilled off to obtain 101 mg (yield: 98%) of the desired product of 2-acetonyl-5,5-dimethyl-2-oxo-1,3,2-dioxaphosphorinane (IV) as colorless solid.
(Melting point: 89°–93° C.

EXAMPLE 4

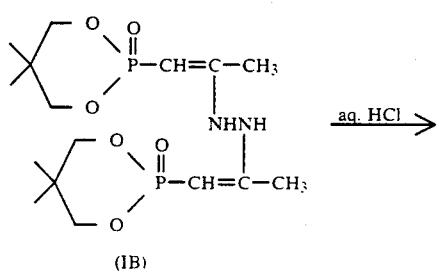

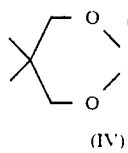

102 mg (0.250 mmol) of the hydrazine derivative (IB) as in Example 2 was suspended in 1.1 g of acetonitrile and dissolved by addition of 2.2 g of 10% by weight hydrochloric acid. The mixture was left for one hour. The reaction solution diluted with 30 ml of 20% by weight sodium chloride aqueous solution, was extracted 2 times with 30 ml of chloroform. The chloroform layers were combined and dried over anhydrous sodium sulfate, followed by filtration. The solvent was distilled off to obtain 101 mg (yield: 98%) of desired product of 2-acetonyl-5,5-dimethyl-2-oxo-1,3,2-dioxaphosphorinane (IV) as colorless solid.
Melting point: 89°–93° C.

EXAMPLE 5

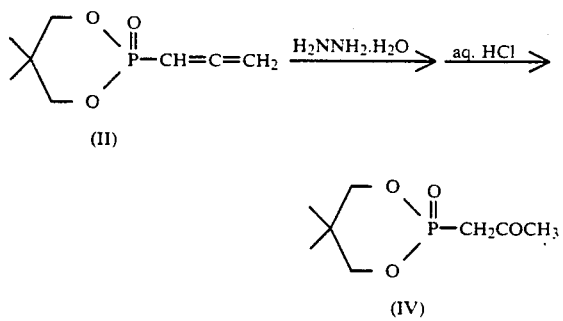

0.69 g (3.7 mmol) of 2-allenyl-5,5-dimethyl-2-oxo-1,3,2-dioxaphosphorinane (II) was dissolved in 3 ml of acetonitrile, and 0.22 g (4.4 mmol) of hydrazine monohydrate was added thereto. The mixture was left for 30 minutes at room temperature. Then, 4.8 g of 10% by weight hydrochloric acid was added thereto and stirred for one hour. The solvent was distilled off to about one-half its initial volume under reduced pressure and the reaction mixture diluted with 30 ml of 20% by weight sodium chloride aqueous solution, was extracted 2 times with 40 ml of chloroform. The chloroform layers were combined and dried over anhydrous sodium sulfate, followed by filtration. The solvent was distilled off to obtain 0.75 g (yield: about quantitative amount) of the desired product of 2-acetonyl-5,5-dimethyl-2-oxo-1,3,2-dioxaphosphorinane (IV) as colorless solid.
Melting point: 89°–93° C.

EXAMPLE 6

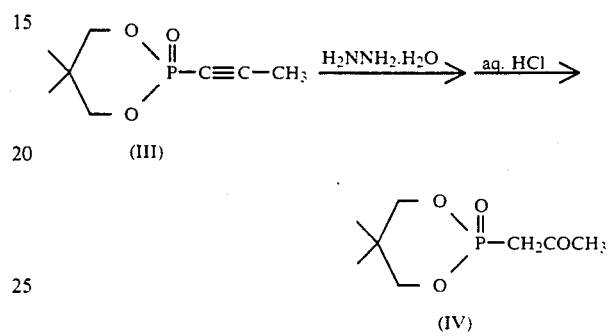

0.69 g (3.7 mmol) of 5,5-dimethyl-2-(1-propynyl)-2-oxo-1,3,2-dioxaphosphorinane (III) was dissolved in 3 ml of acetonitrile, and 0.22 g (4.4 mmol) of hydrazine monohydrate was added thereto. The mixture was left for 30 hours at room temperature. Then, 4.8 g of 10% by weight hydrochloric acid was added thereto and stirred for one hour. The solvent was distilled off to about one-half of its initial volume under reduced pressure, and the reaction mixture diluted with 30 ml of 20% by weight sodium chloride aqueous solution, was extracted 2 times with 40 ml of chloroform. The chloroform layers were combined and dried over anhydrous sodium sulfate, followed by filtration. The solvent was distilled off to obtain 0.77 g (yield: about quantitative amount) of the desired product of 2-acetonyl-5,5-dimethyl-2-oxo-1,3,2-dioxaphosphorinane (IV) as colorless solid.
Melting point: 89°–93° C.

EXAMPLE 7

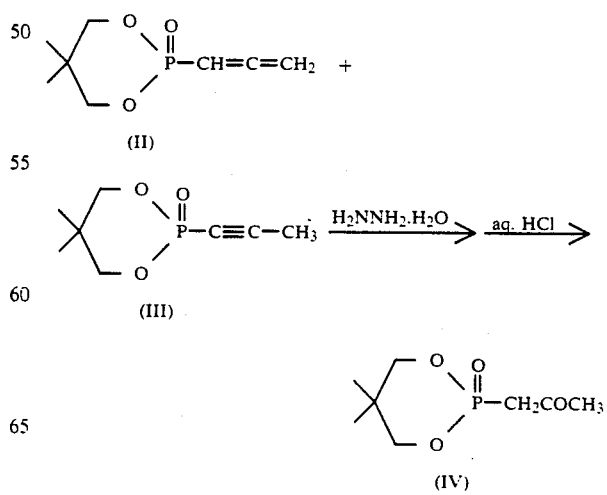

A solution mixture of II and III obtained in Reference Example 1 was stirred under cooling with ice and 510 g (10.2 mol) of hydrazine monohydrate was dropwise added thereto. After the completion of dropwise addition, the solution mixture was stirred for 30 minutes (the reaction was completed in ten minutes), and 11.2 kg of 10% by weight hydrochloric acid was added thereto. The solution mixture was stirred for one hour at room temperature and 5.0 kg of the solvent was distilled off. The solution was subjected to salting-out by addition of 1.38 kg of sodium chloride and extracted 2 times with 15.8 kg of chloroform. The chloroform layers were combined and dried over anhydrous sodium sulfate, followed by filtration. The solvent was distilled off, and the residue was dissolved in 3.5 kg of toluene and cooled with ice. The crystal thus precipitated was collected by filtration by means of suction and washed with 1.0 kg of toluene cooled and dried to obtain 1,000 g (yield: 57.5% through 4 steps) of the desired product of 2-acetonyl-5,5-dimethyl-2-oxo-1,3,2-dioxaphosphorinane as colorless crystal.

Melting point: 89°–93° C.

EXAMPLE 8

(8-1)

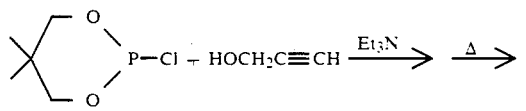

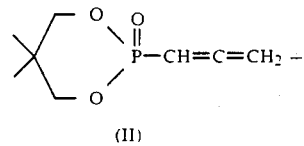

(II)

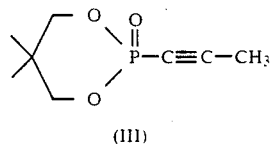

(III)

(8-2)

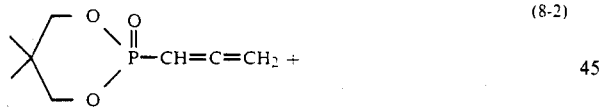

(II)

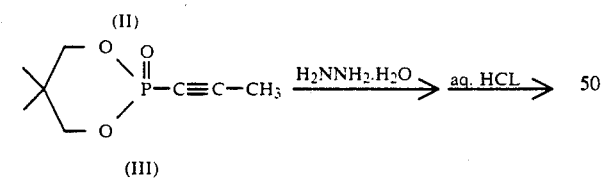

(III)

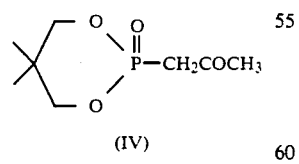

(IV)

25.8 g (255 mmol) of triethylamine and 15.3 g (273 mmol) of propargyl alcohol were dissolved in 201 g of 1,2-dichloroethane, and 42.9 g (254 mmol) of 2-chloro-5,5-dimethyl-1,3,2- dioxaphosphorinane was dropwise added under cooling with ice and stirring (dropwise addition time required: 51 minutes).

After the completion of dropwise addition, the mixture was continued to stir for 3 hours under cooling with ice, and triethylamine hydrochloride thus precipitated was removed by filtration by means of suction. Triethylamine hydrochloride was washed with 54.9 g of 1,2-dichloroethane cooled, and the wash liquid and the filtrate were combined. The combined solution was refluxed for 2 hours under heating to obtain 1,2-dichloroethane solution of a mixture of 2-allenyl-5,5-dimethyl-2-oxo-1,3,2-dioxaphosphorinane (II) and 5,5-dimethyl-2-(1-propynyl)-2-oxo-1,3,2-dioxaphosphorinane (III).

(8-2)

The 1,2-dichloroethane solution of the mixture of 2-allenyl-5,5-dimethyl-2-oxo-1,3,2-dioxaphosphorinane (II) and 5,5-dimethyl-2-(1-propynyl)-2-oxo-1,3,2-dioxaphosphorinane (III) obtained in the above step (8-1) was stirred under cooling with ice, and 15.8 g (316 mmol) of hydrazine monohydrate was gradually added thereto. After stirring for 30 minutes, the solution was returned to room temperature. Then, 121 g (663 mmol) of 20% by weight hydrochloric acid was added thereto after stirring for 17 hours, and further stirred for one hour. The reaction mixture was allowed to stand and subjected to liquid separation to remove the 1,2-dichloroethane layer. The aqueous layer was extracted 3 times with 266 g of dichloroethane. The 1,2-dichloroethane layers were combined and dried over anhydrous sodium sulfate, followed by filtration. The solvent was distilled off and 49 g of crystalline residue was recrystallized from 156 g of toluene to obtain 39.8 g (yield: 75.9%) of the desired product of 2-acetonyl-5,5-dimethyl-2-oxo-1,3,2-dioxaphosphorinane (IV) as colorless crystal.

Melting point: 89°–93° C.

We claim:

1. A hydrazine derivative having the formula:

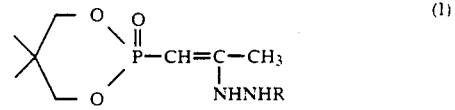

(I)

wherein R is a hydrogen atom or

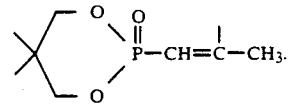

2. A compound of claim 1, wherein R is hydrogen.
3. A compound of claim 1, wherein R is

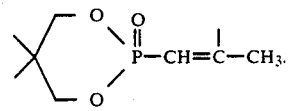

* * * * *